(12) United States Patent
Chamberlain et al.

(10) Patent No.: US 6,388,093 B1
(45) Date of Patent: May 14, 2002

(54) SYNTHESES FOR PREPARING 1,4-DIKETOPYRROLO [3,4-C]PYRROLES

(75) Inventors: Terrence R. Chamberlain, Montgomery, OH (US); Craig Thornley, deceased, late of Moray (GB), by Jack Thornley, executor

(73) Assignee: Sun Chemical Corporation, Fort Lee, NJ (US)

( * ) Notice: Subject to any disclaimer, the term of this patent is extended or adjusted under 35 U.S.C. 154(b) by 0 days.

(21) Appl. No.: 09/755,566

(22) Filed: Jan. 5, 2001

(51) Int. Cl.[7] .............................................. C07D 487/06
(52) U.S. Cl. ...................................................... 548/453
(58) Field of Search ......................................... 548/453

(56) References Cited

U.S. PATENT DOCUMENTS

| | | | |
|---|---|---|---|
| 4,415,685 A | 11/1983 | Iqbal et al. | 524/92 |
| 4,579,949 A | 4/1986 | Rochat et al. | 546/167 |
| 4,585,878 A | 4/1986 | Jost et al. | 548/453 |
| 4,659,775 A | 4/1987 | Pfenninger et al. | 524/92 |
| 4,931,566 A | 6/1990 | Surber et al. | 548/453 |

*Primary Examiner*—T. A. Solola
*Assistant Examiner*—Rebecca Anderson
(74) *Attorney, Agent, or Firm*—Sidney Persley

(57) ABSTRACT

A synthesis for preparing asymmetrical 1,4-diketopyrrolo[3,4-c]pyrroles involving: (a) reacting a β-ketoamide with a strong base; (b) halogenating the same or a different β-ketoamide; (c) reacting the reaction products of step (a) and (b) to form a succinamide; and (d) heating the succinamide in the presence of a Lewis Acid. Symmetrical 1,4-diketopyrrolo [3,4-c]pyrroles are synthesized by oxidatively dimerizing the reaction product of step (b) to form a succinamide; and heating the succinamide in the presence of a Lewis Acid.

17 Claims, No Drawings

SYNTHESES FOR PREPARING 1,4-DIKETOPYRROLO [3,4-C]PYRROLES

BACKGROUND OF THE INVENTION

1. Field of the Invention

The invention relates to syntheses for preparing 1,4-diketopyrrolo[3,4-c]pyrroles useful as pigments or intermediates in the coloration of plastics, paints and printing inks.

2. Description of Related Art

A variety of syntheses exist in the prior art for the preparation of 1,4-diketopyrrolo[3,4-c]pyrroles of the general formula:

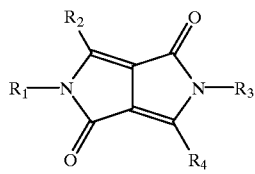

wherein $R_1$ to $R_4$ are commonly used substituent groups such as alkyl or hydrogen. For example, U.S. Pat. No. 4,415,685 discloses preparing a 1,4-diketopyrrolo[3,4-c] pyrrole, where $R_1$ and $R_3$ are hydrogen and $R_2$ and $R_4$ are phenyl, by heating benzonitrile with bromoacetic ester and zinc in toluene. Alternatively, 1,4-diketopyrrolo [3,4-c] pyrrole derivatives where $R_2$ and $R_4$ are different and prepared by subsequently introducing the substituent groups or by converting pre-existing precursor substituent groups via halogenation, acylation, sulfochlorination, etc. which may be followed by reaction of the sulfochloride, for example with an amine, alcohol or phenol.

U.S. Pat. No. 4,579,949 describes a process for preparing structurally similar pyrolopyrroles where $R_2$ and $R_4$ are each independently isocyclic or heterocyclic aromatic radicals by reacting disuccinate with a nitrile of the general formula $R_2$—CN or $R_4$—CN in an organic solvent and strong base at elevated temperatures followed by a hydrolysis step.

U.S. Pat. No. 4,931,566 represents an improvement over the process described in U.S. Pat. No. 4,579,949 wherein the hydrolysis step is carried out in stages.

U.S. Pat. No. 4,659,775 describes a process for preparing these pyrrolopyrroles by reacting an amino ester or pyrrolinone containing the $R_2$ substituent with a nitrile of the general formula $R_4$—CN, where $R_4$ represents an alkyl or aralkyl group or an isocyclic or heterocyclic or aromatic radical, in a strong base and an organic solvent.

U.S. Pat. No. 4,585,878 describes two processes for preparing N-substituted 1,4-diketopyrrolo[3,4-c]pyrroles. The first involves reacting a 1,4-diketopyrrolo [3,4-c]-pyrrole, where $R_1$ and $R_3$ are hydrogen, with a compound containing the radicals replacing $R_1$ and $R_3$ as leaving groups, in an organic solvent. The second method involves reacting a compound of the formula $R_2$—CH=N—$R_3$ or $R_4$—CH=N—$R_1$ or both with a succinic acid diester in a base and organic solvent, then dehydrogenating the resulting product.

An object of the present invention is to provide an m improved synthesis for preparing asymmetrical or symmetrical 1,4-diketo pyrrolo[3,4-c]pyrroles from one or more β-ketoamides.

SUMMARY OF THE INVENTION

The first synthesis of the present invention involves a reaction between a halogenated β-ketoamide and an alkaline metal or alkaline earth salt of a β-ketoamide to produce a succinamide, which is then heated in the presence of a Lewis Acid or acid chloride to produce a 1,4-diketopyrrolo[3,4-c] pyrrole.

The second synthesis of the present invention involves an oxidative dimerization of an alkali metal or alkaline earth salt of a β-ketoamide to form a succinamide, which is then heated in the presence of a Lewis Acid or acid chloride to produce a 1,4-diketopyrrolo[3,4-c]pyrrole. diketopyrrolo[3,4-c]pyrrole.

An advantage of the syntheses of the present invention is the flexibility, in that a wide variety of either symmetrical or asymmetrical 1,4-diketopyrrolo[3,4-c]pyrroles can be produced.

In one aspect, the present invention relates to a synthesis for preparing asymmetrical or symmetrical 1,4-diketo pyrrolo[3,4-c]pyrrole of formula I:

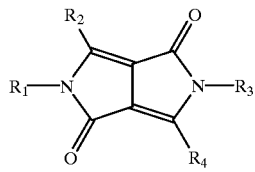

wherein $R_1$, $R_2$, $R_3$ and $R_4$ are each independently selected from hydrogen, $C_1$–$C_2$alkyls, cycloalkyls, aralkyls, or isocyclic or heterocyclic aromatic radicals comprising the steps of:

(a) reacting a β-ketoamide of either formula II:

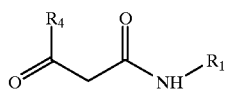

or wherein $R_2$ and $R_4$ are each independently selected from hydrogen, $C_1$–$C_{20}$ alkyls, cycloalkyls, aralkyls, or isocyclic or heterocyclic aromatic radicals or a β-ketoamide of formula III:

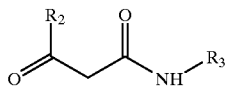

wherein $R_2$ and $R_1$ are each independently selected from hydrogen, $C_1$–$C_{20}$ alkyls, cycloalkyls, aralkyls, or isocyclic or heterocyclic aromatic radicals, with a strong base to form an alkali metal or alkaline earth salt;

(b) halogenating β-ketoamide of formula II or formula III, thereby forming a halogenated β-ketoamide;

(c) reacting said alkali or alkaline earth metal salt with said halogenated β-ketoamide, thereby forming a succinamide of the formula VI:

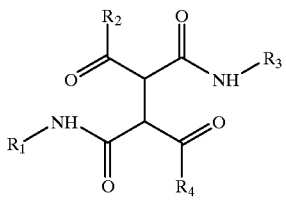

wherein $R_1$ and $R_2$ are each independently selected from hydrogen, $C_1$-$C_{20}$ alkyls, cycloalkyls, aralkyls, or isocyclic or heterocyclic aromatic radicals;

(d) heating the succinamide of Formula IV in the presence of a Lewis acid or acid chloride.

In another aspect, the present invention relates to a synthesis for preparing a symmetrical 1,4-diketopyrrolo[3,4-c]pyrrole conforming to formula V:

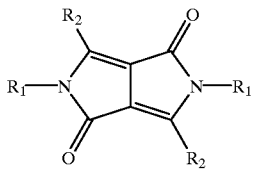

wherein $R_1$ and $R_s$ are as previously defined; comprising the steps of:

(a) reacting a β-ketoamide conforming to formula II:

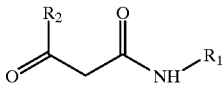

wherein $R_4$ and $R_1$ are each independently selected from hydrogen, $C_1$–$C_{20}$ alkyls, cycloalkyls, aralkyls, or isocyclic or heterocyclic aromatic radicals with a strong base to form an alkali or alkaline earth metal salt;

(b) oxidatively dimerizing said alkali or alkaline earth metal salt, thereby forming a succinamide of formula VI:

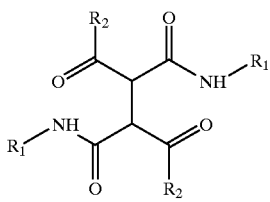

wherein $R_1$, $R_2$, $R_3$ and $R_4$ are each independently selected from hydrogen, $C_1$–$C_{20}$ alkyls, cycloalkyls, aralkyls, or isocyclic or heterocyclic aromatic radicals; and (c) heating said succinamide of formula IV in the presence of a Lewis Acid or acid chloride to effect ring closure.

DETAILED DESCRIPTION OF THE PREFERRED EMBODIMENTS

Step (a) of the asymmetrical of symmetrical synthesis of the present invention comprises reacting a β-ketoamide conforming to either formula II or III with a strong base to form an alkali metal or alkaline earth metal salt β-ketoamide. This reaction IV may be conducted in a non-reactive organic solvent at temperatures of from about 20 to about 140° C., more preferably 20 to 100° C. The particular temperature employed for forming of the metal β-ketoamide salt will depend on the temperature required to solubilize the amide.

Suitable non-reactive organic solvents include n-octane, n-decane, benzene, ethylbenzene, toluene, xylene, chlorobenzene, decalin and the like.

As for the strong base, examples include alkali metal hydroxides such as sodium, potassium and lithium hydroxide; alkaline earth metal hydroxides such as calcium and magnesium hydroxide; alkali metal amides such as sodium, potassium and lithium amide, diethylamide, diisopropylamide or isopropylcyclo-hexylamide; and alkali metal hydrides such as sodium, potassium or lithium hydride, as well as alkali metal or alkaline earth metal alcoholates derived from primary, secondary or tertiary $C_1$–$C_{10}$ alcohols e.g. sodium, potassium or lithium methylate, ethylate, n-propylate, isopropylate, n-butylate, sec-butylate, tert-butylate, 2-methyl-2-butylate, 2-methyl-2-pentylate, 3-methyl-3-pentylate, 3-ethyl-pentylate, or alkali metal or alkaline earth metal phenolates, o-alkyl substituted phenolates, such as sodium or potassium o-cresolate.

It is preferred to use an alkali metal amide, hydride or alcoholate to form the metal amide salt and it is particularly preferred that the alkali metal be sodium or potassium. If alcoholates are employed, it is preferred that the alcohol moiety be derived from a secondary or tertiary alcohol such as isopropyl alcohol, sec- or tert-butyl alcohol and tert-amyl alcohol. If desired, the alkali metal alcoholates may be prepared in situ by reacting the appropriate alcohol with the desired alkali metal, alkali metal hydride or alkali metal amide.

The starting material for step (a) of the first synthesis is a β-ketoamide of either formula II:

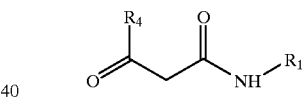

or formula III:

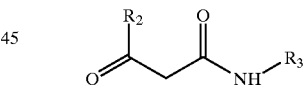

where $R_1$, $R_2$, $R_3$ and $R_4$ are each independently selected from hydrogen, $C_1$–$C_{20}$ alkyls, cycloalkyls, aralkyls, or isocycloic or heterocyclic aromatic radicals.

An important advantage of the syntheses disclosed herein is that they are very versatile. More particularly, the choice of the $C_1$–$C_{20}$ radicals for $R_1$, $R_2$, $R_3$ and $R_4$ is virtually unlimited. Such choices include substituted and unsubstituted straight and branched chain, saturated or unsaturated alkyls, cycloalkyls, aralkyls, isocyclic aromatic and heterocyclic aromatic radicals. Preferably, $R_1$ and $R_3$ are independently selected from hydrogen, $C_6$–$C_{14}$ aryl or aralkyl radicals and $R_2$ and $R_4$ are independently selected from $C_6$–$C_{14}$ aryls or aralkyl radicals.

As alkyl radicals, the preferable choices are $C_1$–$C_{10}$ alkyl radicals especially preferred are $C_1$–$C_{16}$ alkyl radicals such as methyl, ethyl, isopropyl, sec-butyl, tert-butyl, tert-amyl, cyclohexyl, octyl, decyl, dodecyl, stearyl and the like. The aralkyl radical substituents are preferably those which contain a branched or unbranched $C_1$–$C_{12}$ alkyls or alkenyls preferably $C_1$–$C_6$ and especially preferred are $C_1$–$C_4$ and mono- to tetra-cyclic aryl radicals, e.g. benzyl, phenylethyl, etc.

The isocyclic aromatic radical substituents may be mono- to tetra-cyclic radicals, e.g. phenyl, biphenyl, naphthyl, etc. In the case of the heterocyclic aromatic radicals, they may be mono-, di- or tri-cyclic and may be purely heterocyclic, e.g. O-heterocyclic, N-heterocyclic or S-heterocyclic or may contain one or more fused benzene rings, examples include pyridyl, pyrimidyl, pyrazinyl, triazinyl, furyl, pyrrolyl, thiophenyl, quinolyl, coumarinyl, benzofuranyl, benzimidazolyl, benzoxazolyl, dibenzfuranyl, benzothiophenyl, dibenzothiophenyl, indolyl, carbazolyl, pyrazolyl, imidazolyl, oxazolyl, isoxazolyl, thiazolyl, indazolyl, benzthiazolyl, pyridazinyl, cinnolyl, quinazolyl, quinoxalyl, phthalazinyl, phthalazindionyl, phthalamidyl, chromonyl, naphtholactamyl, quinolonyl, o-sulfobenzimidyl, maleinimidyl, naphtharidinyl, benzimidazolonyl, benzoxazolonyl, benzthiazolonyl, benzthiazothionyl, quinazolonyl, quinoxalonyl, phthalazonyl, dioxopyrimidinyl, pyridonyl, isoquinolonyl, isoquinolinyl, isothiazolyl, benzisoxazolyl, benzisothiazolyl, indazolonyl, acridinyl, acridonyl, quinazolindionyl, quinoxalindionyl, benzoxazindionyl, benzoxazinonyl and naphthalimidyl.

Both the isocyclic and heterocyclic aromatic radicals may contain the customary substituents such as halogen atoms; branched or unbranched $C_1$–$C_{20}$ alkyl groups which in turn may contain substituents such as halogen, hydroxyl, cyano, —OCOR, —OR, —COOR, —CONR, —R—OCONHR, etc.; ether groups; mercapto groups; cyano; amino groups; ester groups; ketone groups; amide groups; urethane groups; ureido groups; sulfonylamino groups; sulfonyl groups; carbamoyl groups; —$SO_2R$ groups; sulfamoyl groups and the like.

The β-ketoamide starting materials may be prepared by several known methods. For example, suitable β-ketoamide may be prepared by reaction of an appropriate β-keto ester and an appropriate primary amine. A suitable β-keto ester would have a chemical structure conforming to formula VIII:

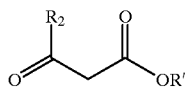

where $R_2$ has the same definition as $R_2$ in formula III, and R' is a $C_1$–$C_{20}$ branched or straight alkyl radical such as methyl, ethyl, propyl, isopropyl, n-butyl, sec-butyl, n-amyl, isoamyl, n-octyl, n-decyl, isodecyl, dodecyl and hexadecyl; and more preferably is a $C_1$–$C_6$ straight chain radical such as methyl, ethyl, propyl or isopropyl.

β-keto esters may be prepared by the well-known Claison Acylation, illustrated by the reaction:

$(R_2)COCH_3+(R_1)_2CO \rightarrow (R_2)COCH_2CO_2(R_1)+(R_1)OH$ where $R_1$ and $R_2$ are as defined above.

The β-keto ester may be reacted with a primary amine having the formula $H_2N$-$R_3$, where $R_3$ is as defined in formula III above, to produce the desired β-ketoamide. The reaction of the β-keto ester and primary amine may be performed at temperatures of from about 40° to about 150° C., more preferably from about 60° to about 100° C., and in the presence of a non-reactive aliphatic or aromatic solvent. The reaction typically has a duration of about 0.5 to 3 hours.

Suitable non-reactive aliphatic or aromatic solvents include hydrocarbons such as n-octane, n-decane, benzene, a toluene, ethylbenzene, chlorobenzene, xylene and decalin.

Alternatively, the desired β-ketoamide starting material may be prepared by reacting a ketone and an isocyanate as illustrated below:

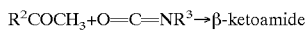

wherein $R^2$ and $R^3$ are as previously defined.

The reaction of the ketone and the isocyanate is typically performed in the presence of a non-reactive diluent.

Step (b) of the first synthesis comprises halogenating a β-ketoamide of either formula II or formula III which was not converted into an alkali metal or alkaline earth metal salt in step (a) above, thereby forming a halogenated β-ketoamide conforming to either formula IX:

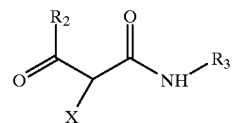

or formula X:

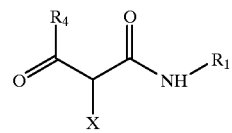

where $R_1$, $R_2$, $R_3$ and $R_4$ have the same definitions as in formulae II and III, respectively, and X is a halogen such as fluorine, chlorine, bromine or iodine.

The halogenating agent may be chlorine, bromine or iodine and the halogenation reaction may be performed at temperatures of about 40° to about 150° C. in the presence of an inert solvent. Suitable examples of inert solvents include carboxylic acids and esters such as acetic acid and ethyl acetate; $C_1$–$C_6$ alcohols such as methanol, ethanol, isopropanol and sec-butanol; and hydrocarbons such as hexane, benzene and chlorobenzene.

Step (c) of the first synthesis comprises reacting the alkali or alkaline earth metal salt formed in step (a) with the halogenated β-ketoamide formed in step (b), thereby forming a succinamide conforming to formula IV:

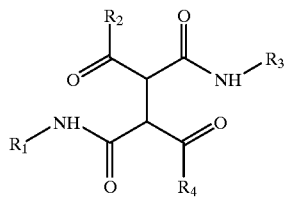

wherein $R_1$, $R_2$, $R_3$ and $R_4$ are as previously defined.

This reaction readily takes place at temperatures ranging from about 40° to about 150° C. and in the presence of a non-reactive solvent such as n-octane, n-decane, benzene, toluene, ethylbenzene, xylene, chlorobenzene, and decalin.

Step (d) of the first synthesis is a ring closure reaction which comprises heating the succinamide produced in step (c) in the presence of a Lewis Acid or acid chloride to thereby produce a 1,4-diketopyrrolo[3,4-c]pyrrole. The reaction will be generally carried out at temperatures ranging from about 80 to about 250° C., more preferably from about 100 to about 220° C., in the presence of a non-reactive organic solvent such as n-octane, n-decane, benzene, toluene, dimethyl formamide, dihydroxyacetone, sulfolene, ethylbenzene, xylene, chlorobenzene and decalin. The preferable Lewis Acid is zinc chloride, zinc acetate, aluminum trichloride or boron trifluoride; the preferred acid chloride is a $C_6$-$C_{14}$ sulfonyl chloride, phosphorus oxychloride or phosphoryl bromide.

The synthesis described above will produce an "asymmetrical" 1,4-diketopyrrolo[3,4-c]pyrrole in which $R_2$ and $R_4$ are always different. One of ordinary skill in the art will readily understand that a "symmetrical" 1,4-diketopyrrolo[3,4-c]pyrrole may be prepared if a single β-ketoamide (i.e., where $R_2$ is identical to $R_4$) is employed for both step (a) and step (b)

The present invention includes a second synthesis directed to the preparation of a symmetrical 1,4-diketopyrrolo[3,4-c]pyrrole conforming to formula V:

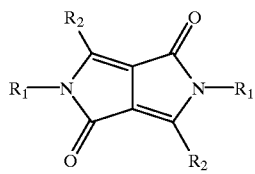

wherein $R_1$ and $R_2$ are independently selected from hydrogen or a $C_1$–$C_{20}$ alkyls, cycloalkyls, aralkyls, or isocyclic or heterocyclic aromatic radicals. This second synthesis includes the steps of:

(a) reacting a β-ketoamide conforming to formula VI:

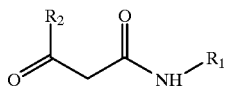

wherein $R_2$ and $R_1$ are each independently selected from hydrogen, $C_1$–$C_{20}$ alkyls, cycloalkyls, aralkyls, or isocyclic or heterocyclic aromatic radicals; with a strong base to form the corresponding alkali metal or alkaline earth salt;

(b) oxidatively dimerizing the alkali metal or alkaline earth salt to form a succinamide conforming to formula VI:

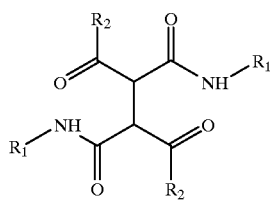

wherein $R_1$ and $R_2$ are as previously defined;

(c) heating said succinamide in the presence of a Lewis Acid or an acid chloride to thereby produce a symmetrical 1,4-diketopyrrolo[3,4-c]pyrrole.

Step (a) of the second synthesis corresponds to step (a) of the first synthesis of the present invention.

Step (b) of the second synthesis may be performed using a halogen such as chlorine, bromine or iodine at temperatures of from about 20° to about 100° C., preferably from about 20° to 60° C. The reaction is preferably carried out in the presence of a non-reactive solvent such as n-hexane, n-octane, n-decane, cyclohexane, benzene, toluene, xylene, ethylbenzene, chlorobenzene and decalin.

Step (c) of the second synthesis involves heating the succinamate resulting from step (b) as described in step (d) of the first synthesis.

The 1,4-diketopyrrolo[3,4-c]pyrroles which may be prepared by the syntheses of the present invention are useful as pigments and pigment intermediates for coloring plastics, resins, paints, lacquers and printing inks using techniques and apparatus well known to those of ordinary skill in this art.

Specific aspects of the syntheses of the present invention are disclosed in even greater detail in the following examples. The examples are illustrative only, and are not intended to limit the scope thereof in any respect. All parts and percentages provided are in weight percent unless otherwise noted.

EXAMPLE 1

Preparation of a β-ketoester

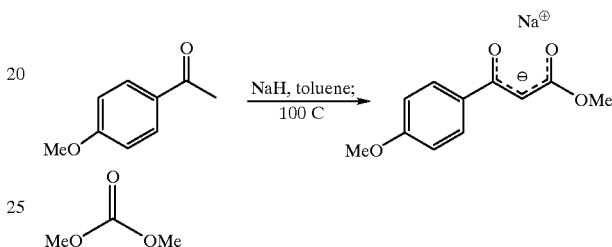

A mixture of dimethylcarbonate (28.5 g, 0.31 mol) and sodium hydride (11.21 g, 80 vol. % suspension, 0.37 mol) in toluene (200 ml) was warmed to 100° C. to form the sodium salt of a dimethylcarbonate. A solution of 4'-methoxyacetaophene (38.20 g, 0.25 mol) in toluene (20 ml) was added portion-wise for over 1 hour. The mixture was then heated at reflux for 3 hours. 34 ml of volatiles were collected and the solution was allowed to cool. The solids were collected by filtration, washed with toluene and heptane then dried to give a methyl 2-sodio-2-(4'-methoxybenzoyl) acetate salt product (44.60 g, 77 wt. %).

EXAMPLE 2

Preparation of a β-ketoamide

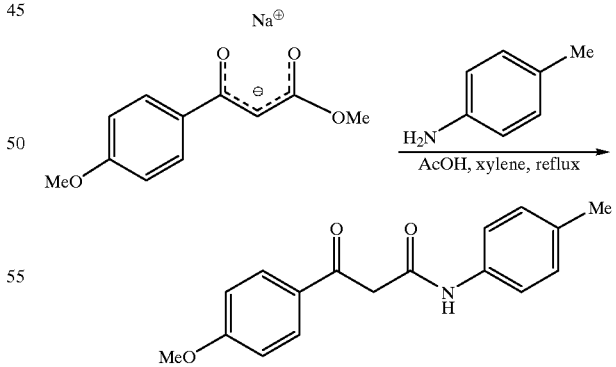

A solution of the methyl 2-sodio-2(4'-methoxybenzoyl) acetate salt prepared in Example 1(44.60 g, 0.194 mol) and 4-toluidine (20.85 g, 0.195 mol) in xylene (300 ml) was stirred and heated over 1 hour. Glacial acetic acid (11.7 g, 0.195 mol) in xylene (100 ml) was added which caused the mixture to become viscous. The mixture was then heated at reflux for 6 hours and allowed to cool to room temperature.

Xylene (200 ml) was added to reduce the viscosity of the mixture. This solution was heated at reflux for 4 hours and allowed to cool to room temperature. The solid N-(4'-methoxybenzoylacetyl)-4-methylaniline product obtained was collected by filtration and washed with toluene and heptane. After removal of the residual organic solvent by drying, the solid product was re-suspended with water (250 ml) and stirred. The solid product was collected by filtration and dried (7.13 g, 13%); m.p. 122–126° C. The solvent was removed from the filtrate. The residue crystallized upon standing and was recrystallized in ethanol to give an additional purified solid product (6.83 g, 12 wt. %); m.p. 127–130° C.

EXAMPLE 3

Preparation of a β-ketoamide

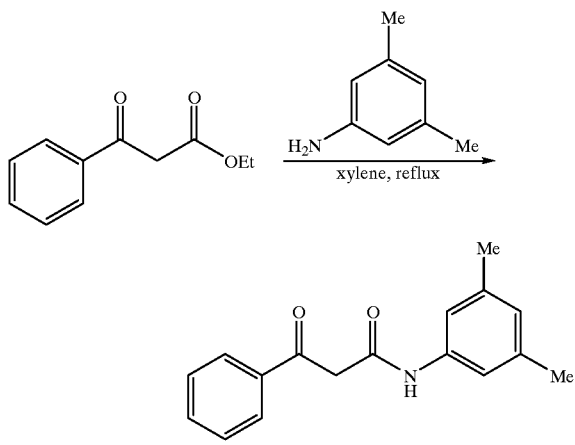

A mixture of ethyl benzoylacetate β-ketoester precursor (53.39 g, 0.25 mol) and 3,5-xylidine (30.45 g, 0.25 mol) in xylene (125 ml) was heated at reflux for 12 hours. The solution was allowed to cool to room temperature then heptane (250 ml) was added while stirring vigorously. The mixture was then set aside for 30 minutes. The precipitated solids were collected by filtration and washed with heptane. The concentration of the mother liquor (to approximately one-quarter volume) followed. Heptane (300 ml) was again added to give additional solids. The combined solids were dried (70–80° C.) to produce the N-(benzoylacetlyl)-3,5-dimethylaniline product (46.27 g, 69 wt. %).

EXAMPLE 4

Preparation of a Halogenated β-ketoamide

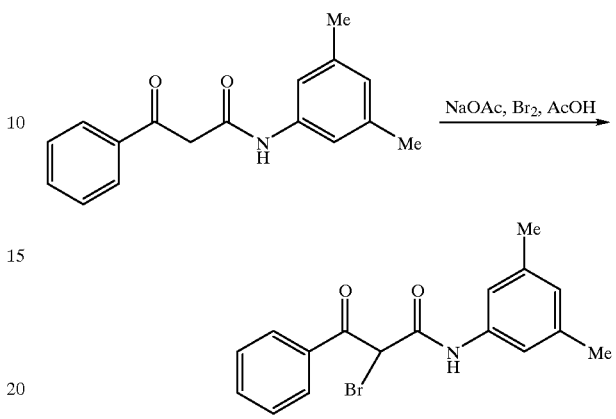

A mixture of N-(bezoylacetyl)-3,5-dimethylanine (26.7 g, 0.10 mol) and anhydrous sodium acetate (9.38 g, 0.11 mol) in glacial acetic acid (250 ml) was stirred under heat until the suspension which formed became homogenous. A solution of bromine (5.9 ml, 0.115 mol) in glacial acetic acid (140 ml) was added dropwise over 30 minutes. The mixture became clear and was stirred at room temperature for 90 minutes, during which time a precipitate began to form. The mixture and precipitate were added to water (800 ml). A gelatinous mass was obtained and collected by decantation, then taken up in ethanol (250 ml). This solution was set aside for 12 hours and some precipitate formed. The remainder of the solids were precipitated by slowly adding water (250 ml). The solids were collected by filtration, washed with water and dried (70° C.) under vacuum for 24 hours to give a N-(2-Benzoyl-2-bromoacetyl)-3,5-dimethlaniline product (31.06 g, 90 wt. %); m.p. 115–121° C.

EXAMPLE 5

Preparation of a Succinamide

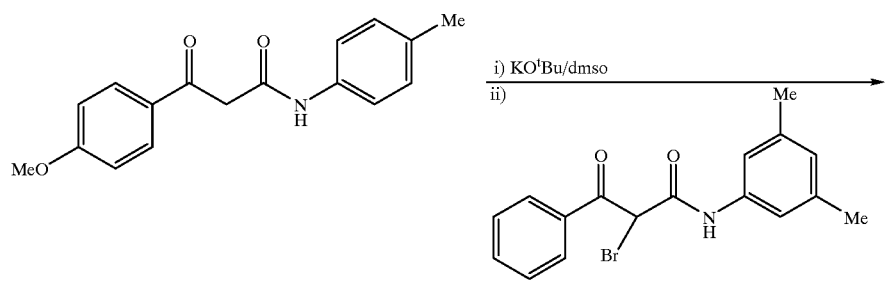

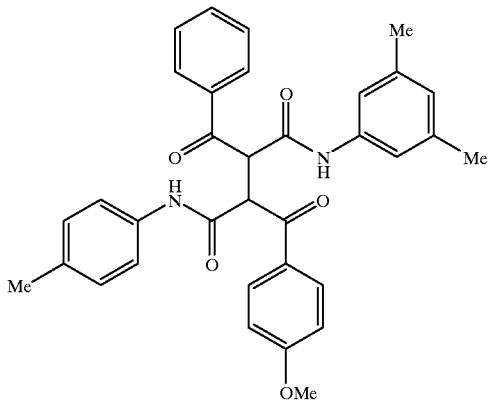

The N-(4'-methoxy benzoylacetyl)-4-methylaniline of Example 2 (1.44 g, 5.09 mmol) was added to a stirred mixture of potassium tert-butoxide. (0.59 g, 5.00 mmol) in dimethoxy sulfonic acid 10 ml) and stirred at room temperature for 15 minutes. The N-(2-benzoyl-2-bromo-acetyl)-3,5-dimethylaniline of Example 1 (1.73 g, 5.00 mmol) was added and the mixture was then stirred for 6 hours at room temperature. The solution was poured into water (60 ml). The resulting precipitate was collected by filtration, washed with water (50 ml) and oven-dried (2.10 g 77 wt. %) , m.p. 174–78° C.(decomp.). (Previous sample, m.p. 220–222° C.)

EXAMPLE 6

1,4 -Diketopyrrolo [3,4-c] pyrrole

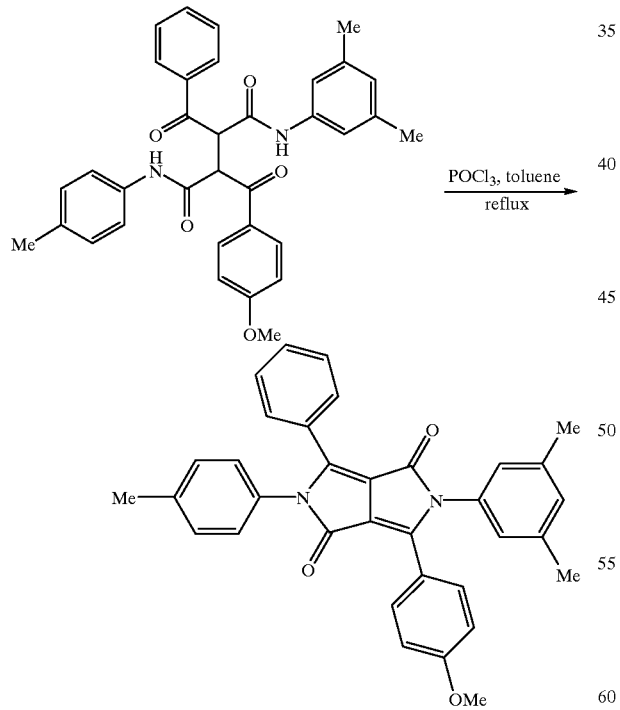

A mixture of the succinamide of Example 5 (0.27 g, 0.5 mmol) and toluene (15 ml) was heated at reflux for 1 hour to remove azeotropic water. The suspension which foamed was allowed to cool and dried under calcium chloride to remove water. Phosphorus oxychloride (0.53 g, 3.5 mmol) was then added. The mixture was heated to reflux and within 10 minutes the solids dissolved and the entire solution became dark red. This dark red solution was heated at reflux for 1 hour and allowed to cool to room temperature. The solvent was removed under vacuum and the resulting dark residue was tritutrated with methanol. The solids were collected by filtration, washed with methanol and dried to yield an orange 1,4-diketo-2-(3'5'-c, dimethylphenyl))-3(4"-methoxyphenyl)-5-(41-methylphenyl)-6-phenylpyrrolo[3,4-c] pyrrole product (0.04 g, 16 wt. %); m.p. 298–310° C.

EXAMPLE 7

1,4-Diketopyrrolo [3,4-c]pyrrole

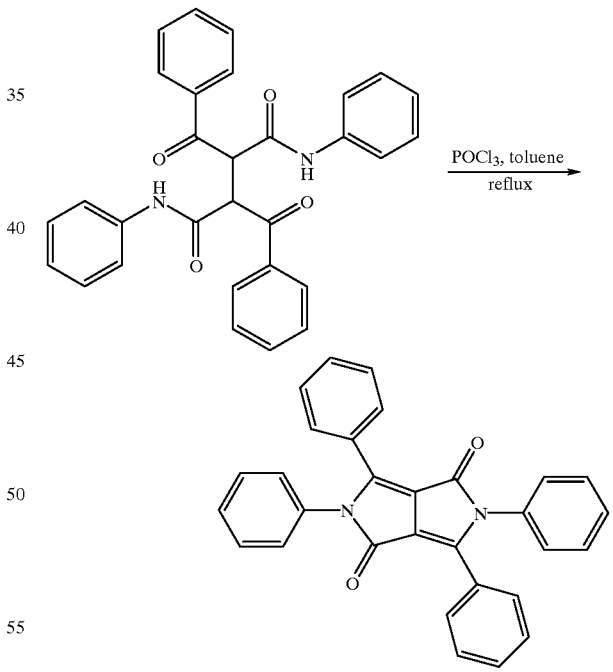

A mixture of the succinamide prepared in Example 5 (3.0g, 6.8 mmol), phosphorous (2.00 g, 13 mmol) and toluene (50 g) was heated at reflux for 1 hour. The mixture was allowed to cool to room temperature and the resulting solids were collected by filtration, washed with toluene and methanol and dried to yield a yellow 1,4-diketo-2,3,5,6-tetraphenylpyrrolo[3,4-c]pyrrole product(2.12 g, 76%), m.p.>300° C.

(Anal. Yield Calculated for $C_{30}H_{20}N_2O_2$: C, 81.82; H, 4.55; N, 6.36. Found: C, 81.62; H, 4.81; N, 6.36.).

EXAMPLE 8

1,4-Diketopyrrolo[3,4-c]pyrrole

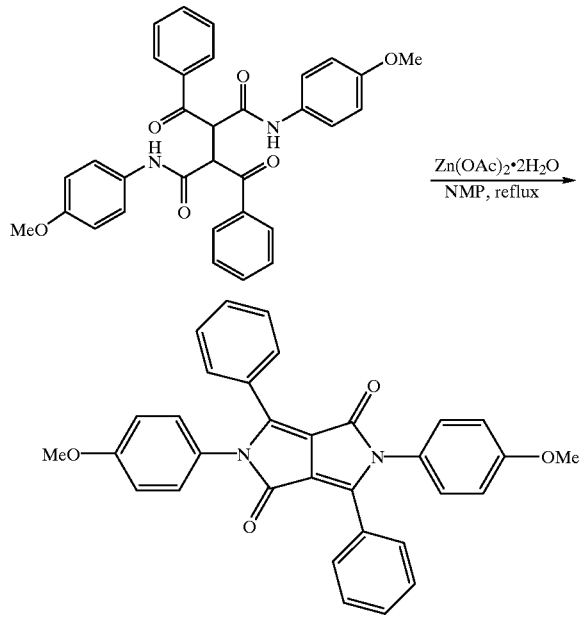

A mixture of the succinamide prepared in Example 5 (3.0 g, 5.6 mmol), zinc acetate dihydrate (2.45 g, 11.2 mmol) and N-methylpyrrolidinone was heated at reflux for 5 hours. The resulting solids were collected by filtration, washed successively with the N-methyl pyrrolidinone solvent and methanol and dried to yield an orange 1,4-Diketo-2,5-di(4, methoxyphenyl)-3,6-diphenylpyrrolo[3, 4-c]pyrrole solid di (4' methoxyphenyl)-3,6-diphenylpyrrolo [3, 4-c]pyrrole solid product (1.29 g, 46%); m.p.>300° C.

(Anal. Calculated for $C_{32}H_{24}N_2O_4$: C, 76.80; H, 4.8; N. 5.60. Found: C, 76.76; H, 5.00; N, 5.49.).

EXAMPLE 9

1,4-diketopyrrolo[3,4-c]pyrrole

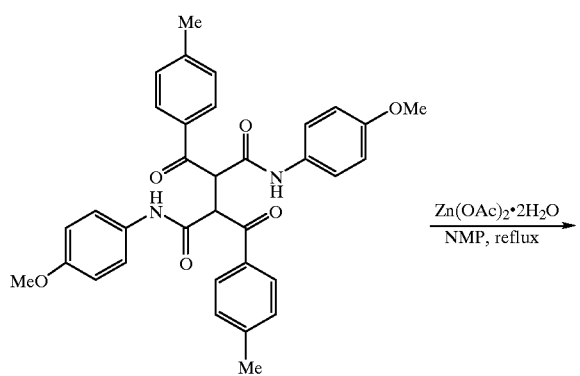

A mixture of the succinamide prepared in Example 5 (52.44g, 93 mmol), zinc acetate dehydrate (51.64 g, 0.235 mol) and N-methylpyrrolidinone (400 g) was heated at reflux for 7 hours. The resulting solids were collected by filtration, washed successively with water and methanol then dried to yield a yellow-orange 1,4-diketo-2,5-di(41-methoxyphenyl)-3,6-di -(4'-methylphenyl) pyrrolo[3,4-c] pyrrole product (25.349, 52%); m.p.>300° C. (Anal. Calculated for $C_{34}H_{28}N_2O_4$: C, 77.27; H, 5.30; N, 5.30. Found: C, 77.17; H, 5.31; N, 5.21).

Those skilled in the art having the benefit of the teachings of the present invention as hereinabove set forth, can effect numerous modifications thereto. These modifications are to be construed as being encompassed within the scope of the present invention as set forth in the appended claims.

What is claimed is:

1. A synthesis for preparing an asymmetrical or symmetrical 1,4-diketopyrrolo[3,4-c]pyrrole of formula I:

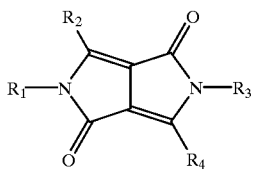

wherein $R_1$, $R_3$, $R_2$, and $R_4$ are each independently selected from hydrogen, $C_1$–$C_{20}$ alkyls, cycloalkyls, aralkyls, or isocyclic or heterocyclic aromatic radicals; comprising the steps of:

(a) reacting a β-ketoamide of either formula II:

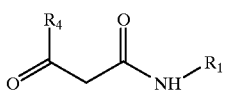

or, alternatively, a β-ketoamide of formula III:

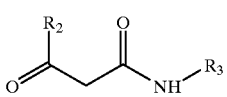

with a strong base to form an alkali metal or alkaline earth metal salt, wherein $R_1$, $R_2$, $R_3$ and $R_4$ are as previously defined;

(b) halogenating a β-ketoamide of either formula II or formula III thereby forming a halogenated β-ketoamide;

(c) reacting said alkali metal or alkaline earth salt formed in step (a) with said halogenated β-ketoamide, thereby forming a succinamide of the formula IV:

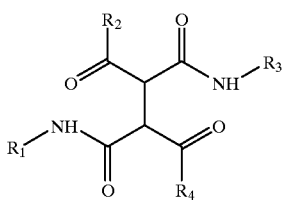

wherein $R_1$, $R_2$, $R_3$ and $R_4$ are as previously defined;

(d) heating the succinamide in the presence of a Lewis Acid or acid chloride to produce said 1,4-diketopyrrolo[3,4-c]pyrrole.

2. The synthesis of claim 1 wherein $R_1$ and $R_3$ are each independently selected from the group consisting of hydrogen, $C_6$–$C_{14}$ aryls and $C_6$–$C_{14}$ aralkyl radicals.

3. The synthesis of claim 1 wherein $R_2$ and $R_4$ are each independently selected from the group consisting of $C_6$–$C_{14}$ aryls and $C_6$–$C_{14}$ aralkyl radicals.

4. The synthesis of claim 1 wherein $R_2$ is different from $R_4$.

5. The synthesis of claim 1 wherein $R_2$ is t he same as $R_4$.

6. The synthesis of claim 1 wherein said strong base is selected from the group consisting of alkali metal hydroxides, alkaline earth metal hydroxides, alkali metal amides, alkali metal hydrides, alkali metal alcoholates, alkaline earth alcoholates, alkali metal phenolates and phenolates.

7. The synthesis of claim 6, wherein said strong base is selected from the group consisting of alkali metal amides, alkali metal hydrides and alkali metal alkali metal alcoholates and alkali earth alcoholates.

8. The synthesis of claim 1 wherein step (c) is performed at a temperature of from about 40° to about 150° C. in the presence of a non-reactive organic solvent.

9. The synthesis of claim 1 wherein said Lewis Acid is selected from the group consisting of zinc chloride, zinc acetate, aluminum trichloride and boron trifluoride.

10. The synthesis of claim 1 wherein said acid chloride is selected from the group consisting of $C_6$–$C_{14}$ sulfonyl chlorides, phosphoryl oxychloride and phosphoryl oxybromide.

11. The synthesis of claim 1 wherein step (d) is performed at a temperature of from about 80° to about 250° C. in the presence of a non-reactive organic solvent.

12. A synthesis for preparing a symmetrical 1,4-diketopyrrolo[3,4-c]pyrrole of the formula V:

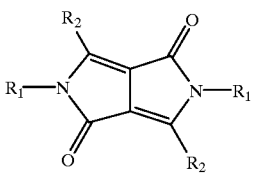

wherein
$R_1$ and $R_2$ are each independently selected from hydrogen, $C_1$–$C_{20}$ alkyls, cycloalkyls, aralkyls, or isocyclic or heterocyclic aromatic radicals; and which synthesis comprises the steps of:
(a) reacting a β-ketoamide of the formula VI:

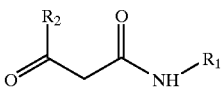

wherein $R_2$ and $R_1$ are as previously defined; with a strong base, thereby forming an alkali or alkaline earth metal salt;
(b) oxidatively dimerizing said alkali or alkaline earth metal salt, thereby forming a succinamide of the formula VII:

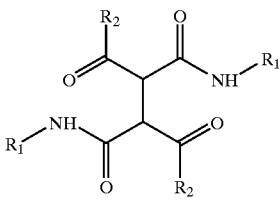

wherein $R_1$ and $R_2$ are as previously defined;
(c) heating said succinamide in the presence of a Lewis acid or acid chloride to effect ring closure.

13. The synthesis of claim 12 wherein $R_1$ and $R_2$ are each independently selected from hydrogen, $C_6$–$C_{14}$ aryls and aralkyl radicals.

14. The synthesis of claim 12 wherein step (b) is performed in the presence of chlorine, bromine or iodine at a temperature ranging from about 20° to about 100° C.

15. The synthesis of claim 12 wherein the Lewis Acid is selected from the group consisting of zinc chloride, zinc acetate, aluminum trichloride and boron trifluoride.

16. The synthesis of claim 11 wherein the acid chloride is selected from the group consisting of $C_6$–$C_{14}$ sulfonyl chlorides, phosphoryl oxychloride and phosphoryl oxybromide.

17. The synthesis of claim 11 wherein step (c) is carried out at temperatures ranging from about 80° to about 250° C. in the presence of a non-reactive organic solvent.

* * * * *

UNITED STATES PATENT AND TRADEMARK OFFICE
CERTIFICATE OF CORRECTION

PATENT NO. : 6,388,093 B1
DATED : May 14, 2002
INVENTOR(S) : Chamberlain et al.

It is certified that error appears in the above-identified patent and that said Letters Patent is hereby corrected as shown below:

<u>Title page,</u>
Item [57], ABSTRACT,
Line 8, "of step (b) to form a" should read -- of step (a) to form a --.

<u>Column 2,</u>
Line 11, "a 1,4-diketopyrrolo[3,4-c]pyrrole.diketopyrrolo[3," should read
-- a 1,4-diketopyrrolo[3, --;
Line 46, "or wherein R2 and R4 are" should read -- or wherein R1 and R4 are --;
Line 57, "wherein R2 and R1 are" should read -- wherein R2 and R3 are --;
Line 67, "of the formula VI:" should read -- of the formula IV: --.

<u>Column 3,</u>
Line 11, "wherein R1 and R2 are" should read -- wherein R1, R2, R3 and R4 are --;
Line 55, "wherein R1, R2, R3 and R4 are" should read -- wherein R1 and R2 are --;
Line 58, "of formula IV in" should read -- of formula VI in --;
Line 67, "This reaction IV may be" should read -- This reaction of VI may be --.

<u>Column 5,</u>
Line 53, "well-known Claison" should read -- well-known Claisen --.

<u>Column 6,</u>
Line 32, "fluorine, chlorine, bromine" should read -- chlorine, bromine --.

<u>Column 7,</u>
Line 7, "in which R2 and R4" should read -- in which R2 and R4 and/or R1 and R2 are --.

<u>Column 8,</u>
Line 32, "was warmed to 100o C. to form the sodium salt of a dimethylcarbonate." should read -- was warmed to 100oC. --.

<u>Column 11,</u>
Line 22, "dimethoxy sulfonic acid" should read -- dimethyl sulfoxide acid --;
Line 29, "174-78 C. (decomp.)(Previous sample, m.p. 220-22C.) should read -- 174-78 C(decomp.). --.

<u>Column 12,</u>
Line 58, "succinamide prepared in" should read -- succinamide as prepared in --.

UNITED STATES PATENT AND TRADEMARK OFFICE
CERTIFICATE OF CORRECTION

PATENT NO. : 6,388,093 B1
DATED : May 14, 2002
INVENTOR(S) : Chamberlain et al.

It is certified that error appears in the above-identified patent and that said Letters Patent is hereby corrected as shown below:

Column 13,
Line 33, "succinamide prepared in" should read -- succinamide as prepared in --.

Column 14,
Line 19, "succinamide prepared in" should read -- succinamide as prepared in --.

Signed and Sealed this

Twenty-sixth Day of November, 2002

*Attest:*

*Attesting Officer*

JAMES E. ROGAN
*Director of the United States Patent and Trademark Office*